(12) United States Patent
Campbell

(10) Patent No.: US 11,219,661 B2
(45) Date of Patent: Jan. 11, 2022

(54) ULCERATIVE COLITIS MEDICATION

(71) Applicant: Paul Campbell, Austin, TX (US)

(72) Inventor: Paul Campbell, Austin, TX (US)

( * ) Notice: Subject to any disclaimer, the term of this patent is extended or adjusted under 35 U.S.C. 154(b) by 199 days.

(21) Appl. No.: 16/747,462

(22) Filed: Jan. 20, 2020

(65) Prior Publication Data

US 2021/0220427 A1    Jul. 22, 2021

(51) Int. Cl.
*A61K 36/9068* (2006.01)
*A61K 36/9066* (2006.01)
*A61K 36/45* (2006.01)
*A61P 1/04* (2006.01)

(52) U.S. Cl.
CPC .......... *A61K 36/9068* (2013.01); *A61K 36/45* (2013.01); *A61K 36/9066* (2013.01); *A61P 1/04* (2018.01)

(58) Field of Classification Search
CPC . A61K 36/45; A61K 36/9066; A61K 36/9068
See application file for complete search history.

(56) References Cited

U.S. PATENT DOCUMENTS

| | | |
|---|---|---|
| 8,691,296 B2 | 4/2014 | Zhang et al. |
| 9,028,888 B2 | 5/2015 | Ghorbani |
| 9,533,019 B1 | 1/2017 | Awaad et al. |
| 2021/0038664 A1* | 2/2021 | Legge ............... A23L 33/21 |

* cited by examiner

*Primary Examiner* — Aaron J Kosar

(57) ABSTRACT

An illustrated side view of an exemplary medication for treating ulcerative colitis is presented. The medication is useful for reducing the risk and debilitation associated with having ulcerative colitis, as well as improving overall health. The medication further is useful for removing life threatening complications such as, but not limited to, perforated colon, liver disease, inflammation of skin, joints and eyes, decreasing the risk of colon cancer while eliminating the need for surgery for relief of the ulcerative colitis. The medication is also inexpensive and all natural.

6 Claims, 2 Drawing Sheets

ULCERATIVE COLITIS MEDICATION

FIELD OF THE INVENTION

This invention relates to medications. More particularly, it relates to medication for ulcerative colitis.

BACKGROUND

Ulcerative colitis (UC) is a long-term condition that results in inflammation and ulcers of the colon and rectum. The primary symptoms of active disease are abdominal pain and diarrhea mixed with blood. Weight loss, fever, and anemia may also occur. Often, symptoms come on slowly and can range from mild to severe. Symptoms typically occur intermittently with periods of no symptoms between flares. Complications may include megacolon, inflammation of the eye, joints, or liver, and colon cancer.

The cause of UC is unknown. Theories involve immune system dysfunction, genetics, changes in the normal gut bacteria, and environmental factors. Rates tend to be higher in the developed world with some proposing this to be the result of less exposure to intestinal infections, or to a Western diet and lifestyle. The removal of the appendix at an early age may be protective. Diagnosis is typically by colonoscopy with tissue biopsies. It is a kind of inflammatory bowel disease (IBD) along with Crohn's disease and microscopic colitis.

Dietary changes, such as maintaining a high-calorie diet or lactose-free diet, may improve symptoms. Several medications are used to treat symptoms and bring about and maintain remission, including aminosalicylates such as mesalazine or sulfasalazine, steroids, immunosuppressants such as azathioprine, and biologic therapy. Removal of the colon by surgery may be necessary if the disease is severe, does not respond to treatment, or if complications such as colon cancer develop. Removal of the colon and rectum can cure the disease.

Together with Crohn's disease, about 11.2 million people were affected as of 2015. Each year it newly occurs in 1 to 20 per 100,000 people, and 5 to 500 per 100,000 individuals are affected. The disease is more common in North America and Europe than other regions. Often it begins in people aged 15 to 30 years, or among those over 60. Males and females appear to be affected in equal proportions. It has also become more common since the 1950s. Together, ulcerative colitis and Crohn's disease affect about three million people in the United States. With appropriate treatment the risk of death appears the same as that of the general population. The first description of ulcerative colitis occurred around the 1850s.

The current medications are not always effective nor have a positive long-term effect on a person's body. The medications are often synthetics or combinations with inert compounds and are expensive to obtain.

In light of the foregoing, there is a need for a medication that relieves the symptoms of ulcerative colitis. There is also a need for an organic medication without synthetic or combinations of inert compounds. Further, the medication should be inexpensive and available over the counter.

DETAILED DESCRIPTION

Figure 1:
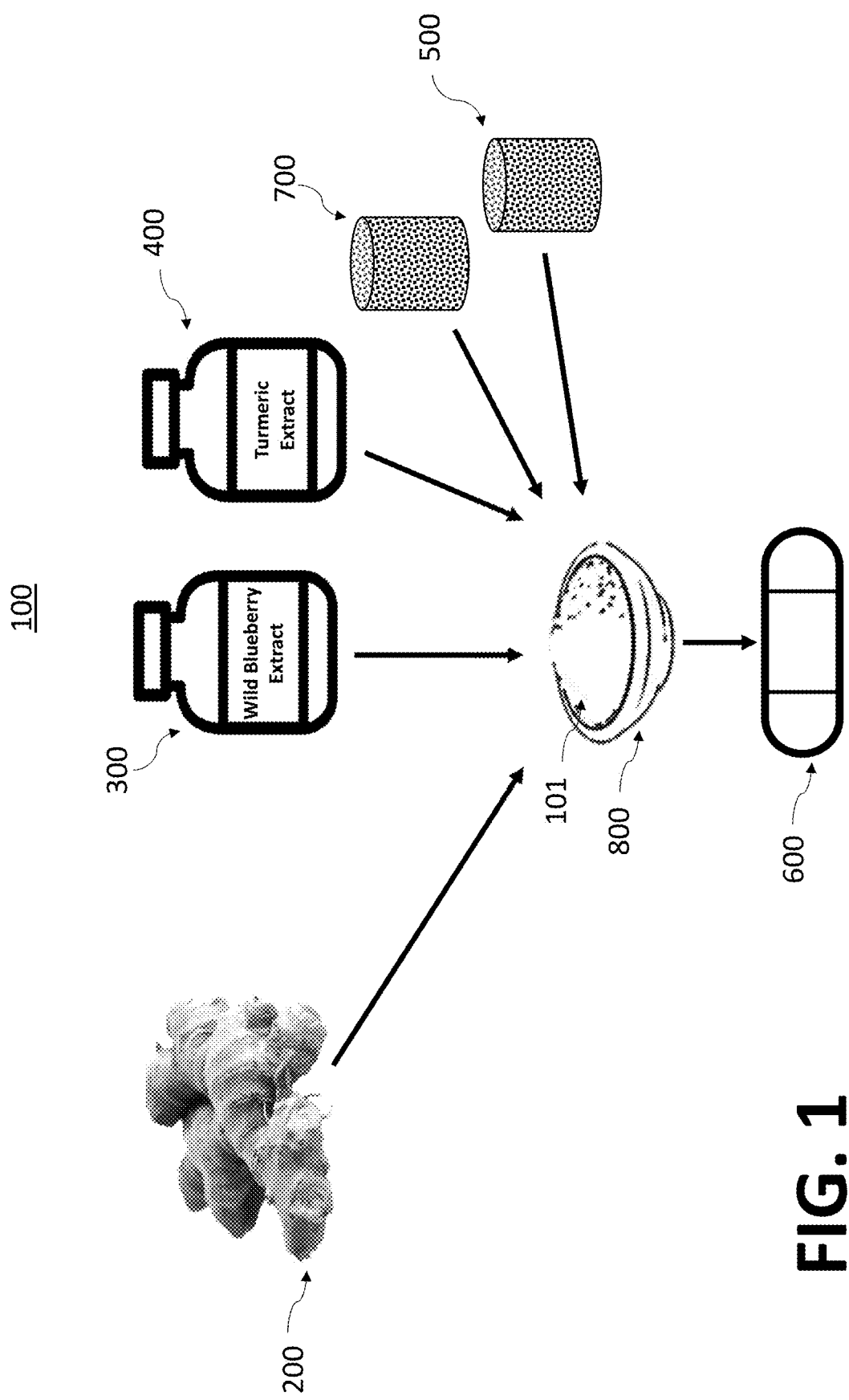
FIG. 1 is an illustrated side view of an exemplary medication.

The phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise. Such terms do not generally signify a closed list.

"Above," "adhesive," "affixing," "any," "around," "both," "bottom," "by," "comprising," "consistent," "customized," "enclosing," "friction," "in," "labeled," "lower," "magnetic," "marked," "new," "nominal," "not," "of," "other," "outside," "outwardly," "particular," "permanently," "preventing," "raised," "respectively," "reversibly," "round," "square," "substantial," "supporting," "surrounded," "surrounding," "threaded," "to," "top," "using," "wherein," "with," or other such descriptors herein are used in their normal yes-or-no sense, not as terms of degree, unless context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to, or combined, without limiting the scope to the embodiments disclosed herein.

Referring to FIG. 1, an illustrated side view of an exemplary medication 100 for treating ulcerative colitis is presented. The medication 100 is useful for reducing the risk and debilitation associated with having ulcerative colitis, as well as improving overall health. The medication 100 further is useful for removing life threatening complications such as, but not limited to, perforated colon, liver disease, inflammation of skin, joints and eyes, decreasing the risk of colon cancer while eliminating the need for surgery for relief of the ulcerative colitis. The medication 100 is also inexpensive and all natural.

The medication 100 has ginger root (rhizome) 200, blueberry extract (vaccinium angustifolium) 300, turmeric extract (rhizome) 400, anticaking agents 700, fillers 500 and a container 600.

The container 600 is preferably a capsule shape, however other shapes are hereby contemplated, including, but not limited to, pill, chewable pill, powder, etc. The container 600 is preferably made of a gelatin material; however, any other type of digestible material may be used. The medication 100 is preferably taken each twelve (12) hours, however other periods of dosage are hereby considered.

The ginger root 200 is preferably in a powder format, however a ginger root may be ground by a grinder, or the like, from a ginger root plant or other formats such as liquid. The ginger root 200 is preferably an amount of one-thousand six-hundred fifty milligrams (1650 mg) or one and sixty-five hundredths (1.65) grams, however other amounts of ginger root 200 are hereby contemplated, including, but not limited to, one-thousand four-hundred milligrams (1400 mg), two-thousand milligrams (2000 mg), etc.

The blueberry extract 300 is preferably in a powder format, however other formats are hereby contemplated such as liquid. The blueberry extract 300 is preferably an amount of one-thousand five-hundred milligrams (1500 mg)

or one and one-half (1.5) grams, however other amounts of blueberry extract 300 are hereby contemplated, including, but not limited to, one-thousand milligrams (1000 mg), two-thousand milligrams (2000 mg), etc. The blueberry extract 300 is preferably powder when acquired, however means for processing blueberry extract 300 into a powder is hereby contemplated.

The turmeric extract 400 is preferably in a powder format, however other formats are hereby contemplated such as liquid. The turmeric extract 400 is preferably an amount of one-thousand two-hundred milligrams (1200 mg) or one and two tenths (1.2) grams, however other amounts of turmeric extract 400 are hereby contemplated, including, but not limited to, one-thousand milligrams (1000 mg), one-thousand five-hundred milligrams (1500 mg), etc. The turmeric extract 400 is preferably powder when acquired, however means for processing turmeric extract 400 into a powder is hereby contemplated.

Other fillers 500 are preferably in powder format, however other formats are hereby contemplated such as liquid. The fillers 500 are inert in effect and are useful for providing dietary fiber, bulk or some other non-nutritive purpose.

Anti-caking agents 700 are preferably in powder format, however other formats are hereby contemplated such as liquid. Anti-caking agents 700 are useful for preventing the formation of lumps (caking) and for easing packaging, transport, flowability, and consumption.

The ginger root (rhizome) 200, blueberry extract (vaccinium angustifolium) 300, turmeric extract (rhizome) 400, anticaking agents 700 and fillers 500 are all obtained for the medication 100. Preferably the ginger root 200, in an amount of one-thousand six-hundred fifty milligrams (1650 mg) is added to a vessel 800. The blueberry extract 300, preferably in an amount of one-thousand five-hundred milligrams (1500 mg), is added to the vessel 800. Next, the turmeric extract 400, preferably in an amount of one-thousand two-hundred milligrams (1200 mg), is added to the vessel 800. The filling agents 500 and anti-caking agents 700 are further added to the vessel 800.

The vessel 800 is then manipulated such that the ginger root (rhizome) 200, blueberry extract (vaccinium angustifolium) 300, turmeric extract (rhizome) 400, anticaking agents 700 and fillers 500 are substantially well mixed as to have the ginger root (rhizome) 200, blueberry extract (vaccinium angustifolium) 300, turmeric extract (rhizome) 400, anticaking agents 700 and fillers 500 mixed to be significantly uniformly dispersed in the vessel 800. Thus, a mixture of ingredients 101 are contained in the vessel 800.

The mixture of the ingredients 101 in the vessel 800 are the ginger root (rhizome) 200, blueberry extract (vaccinium angustifolium) 300, turmeric extract (rhizome) 400, anticaking agents 700 and fillers 500) are then dispensed into the container 600. The container 600 is then sealed to be a desired dose of the mixture of ingredients 101 in the container 600.

Figure 2B:
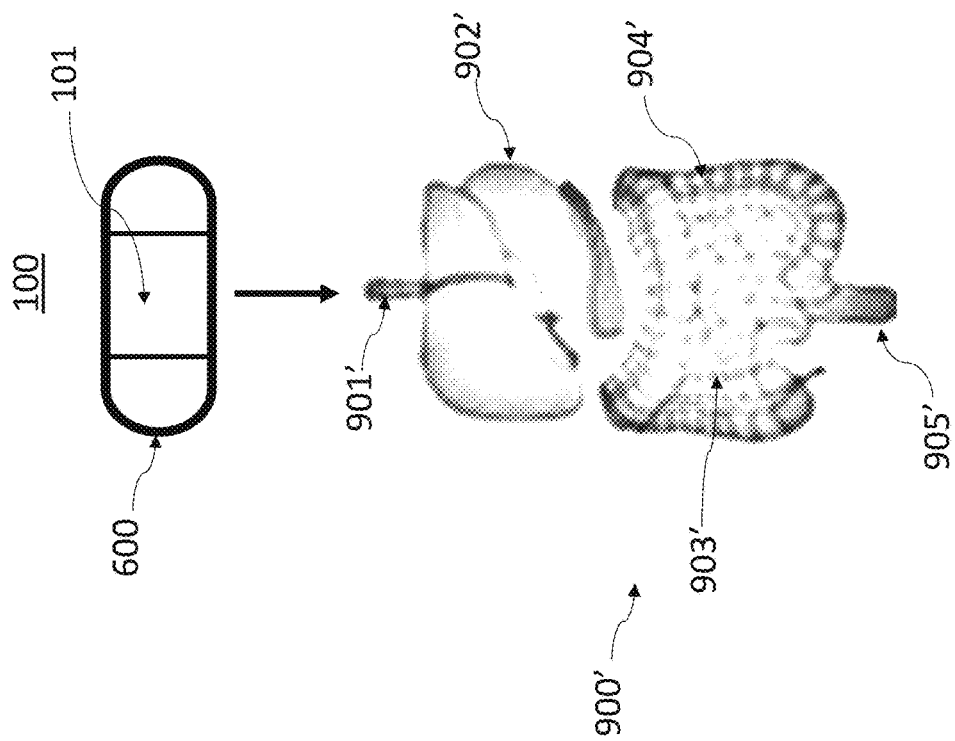
FIG. 2B is an illustrated view of the digestive tract shown in FIG. 2A after use of the medication shown in FIG. 1.
Figure 2A:
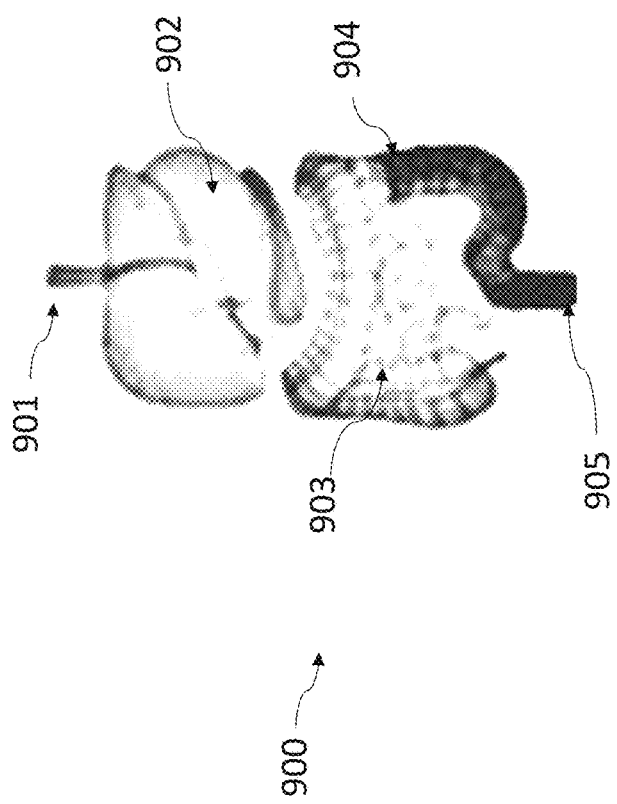
FIG. 2A is an illustrated view of a digestive tract showing ulcerative colitis shown in FIG. 1.

Moving now to FIG. 2A and FIG. 2B, an illustrate view of a digestive tract 900, 900' of a person (not shown) showing a before and after taking a dose of the medication 100 is presented. The FIG. 2A presents the digestive tract 900 which has ulcerative colitis disease. The digestive tract 900 has an esophagus 901, a stomach 902, a small intestine 903, a large intestine 904 and a colon 905. The ulcerative colitis is shown in black in the large intestine 904 and the colon 905 of the digestive tract 900.

The person ingests the container 600. Thus, the mixture of ingredients 101 is passed from through the esophagus 901 into the stomach 902 and passing to the small intestines 903 for absorption into a blood stream (not shown) of the person. After the mixture of ingredients 101 has entered into the blood stream, the mixture of ingredients 101 is directed to provide relief and healing of the ulcerative colitis disease.

In FIG. 2B, the digestive tract 900' has the esophagus 901', a stomach 902', a small intestine 903', a large intestine 904' and a colon 905'. After the mixture of ingredients 101 has taken affect, the large intestine 904' and the colon 905' are clear of the disease as shown by the non-darken aspects of the large intestine 904' and the colon 905'.

In the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

The features described with respect to one embodiment may be applied to other embodiments or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medication for treating ulcerative colitis, the medication comprising:
   a container;
   ginger root, the ginger root being in a powder format;
   turmeric extract, the turmeric extract being in a powder format;
   blueberry extract, the blueberry extract being in a powder format;
   an anti-caking agent, the anti-caking agent being in a powder format; and
   a filler, the filler being in a powder format;
   the ginger root, turmeric extract, the blueberry extract, the anti-caking agent and the filler being mixed and dispersed significantly evenly in a vessel, wherein contents of the vessel being dispensed into the container.

2. The medication of claim 1, wherein the ginger root being an amount of one-thousand six-hundred fifty (1650) milligrams.

3. The medication of claim 1, wherein the blueberry extract being an amount of one-thousand five-hundred (1500) milligrams.

4. The medication of claim 1, wherein the turmeric extract being an amount of one-thousand two-hundred (1200) milligrams.

5. The medication of claim 1, wherein the container being a capsule shape.

6. The medication of claim 1, wherein the container being made of a gelatin material.

\* \* \* \* \*